(12) United States Patent
Tendo et al.

(10) Patent No.: US 7,132,573 B2
(45) Date of Patent: Nov. 7, 2006

(54) AMINE DERIVATIVE

(75) Inventors: Atsushi Tendo, Saitama (JP); Toshihiro Takahashi, Saitama (JP); Tomio Yamakawa, Chiba (JP)

(73) Assignee: Nippon Chemipher Co., Ltd. (JP)

( * ) Notice: Subject to any disclaimer, the term of this patent is extended or adjusted under 35 U.S.C. 154(b) by 87 days.

(21) Appl. No.: 10/527,153

(22) PCT Filed: Sep. 9, 2003

(86) PCT No.: PCT/JP03/11468

§ 371 (c)(1),
(2), (4) Date: Mar. 9, 2005

(87) PCT Pub. No.: WO2004/024672

PCT Pub. Date: Mar. 25, 2004

(65) Prior Publication Data

US 2005/0288530 A1    Dec. 29, 2005

(30) Foreign Application Priority Data

Sep. 11, 2002    (JP)  ............................. 2002-265335

(51) Int. Cl.
*C07C 217/08*    (2006.01)
*C07C 213/08*    (2006.01)
(52) U.S. Cl. .................................................. 564/508
(58) Field of Classification Search ................ 564/508
See application file for complete search history.

(56) References Cited

U.S. PATENT DOCUMENTS 3,640,855 A * 2/1972 Bakker ...................... 508/375

3,796,756 A * 3/1974 Bakker ...................... 564/508

FOREIGN PATENT DOCUMENTS

WO    WO-99/11640 A1    3/1999

OTHER PUBLICATIONS

International Search Report dated Oct. 21, 2003 Application No. PCT/JP03/11468.

* cited by examiner

*Primary Examiner*—Brian Davis
(74) *Attorney, Agent, or Firm*—Nixon Peabody LLP; Jeffrey L. Costellia

(57) ABSTRACT

The invention relates to (1S)-1-isobutoxymethyl-3-methyl-butylamine useful as an intermediate in the synthesis of sodium (2S,3S)-3-[[(1S)-1-isobutoxymethyl-3-methylbutyl]carbamoyl]oxirane-2-carboxylate and a process for production thereof. The process comprises reacting L-leucinol with a compound represented by the following formula in the presence of a base and reducing the obtained (1S)-1-(2-methyl-2-propenoxymethyl)-3-methylbutyl-amine:

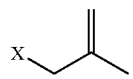

[in which X is a leaving group].

3 Claims, No Drawings

AMINE DERIVATIVE

This application is a 371 of PCT/JP03/11468 filed Sep. 9, 2003.

FIELD OF THE INVENTION

The present invention relates to an amine derivative and a process of production thereof.

BACKGROUND OF THE INVENTION

The under-illustrated sodium (2S,3S)-3-[[(1S)-1-iso-butoxymethyl-3-methylbutyl]carbamoyl]oxirane-2-carboxylate (hereinafter referred to as Compound A) shows a cathepsin-inhibitory action and is useful as a remedy for treating rheumatoid arthritis and osteoporosis (Patent reference 1: WO 99/11640 pamphlet):

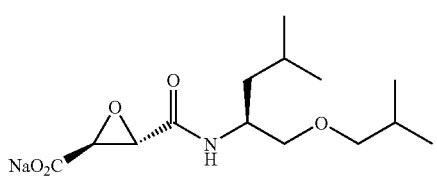

Patent reference 1 describes a process for producing Compound A according to the following reaction scheme (see Example 48 of Patent reference 1):

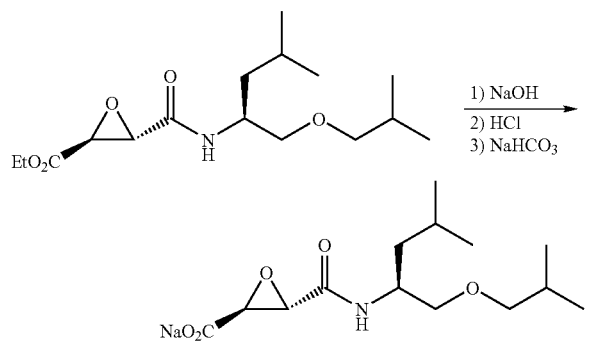

There is a need to provide an industrially employable synthesis process for the production of Compound A.

DISCLOSURE OF THE INVENTION

The present invention has an object to provide an amine derivative employable as an intermediate compound for the synthesis of Compound A. The amine derivative is (1S)-1-isobutoxymethyl-3-methylbutylamine represented by the following formula:

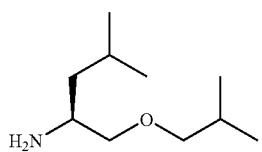

The invention also has an object to provide a process for producing the amine derivative.

The (1S)-1-isobutoxymethyl-3-methylbutylamine can be obtained according to the following reaction scheme:

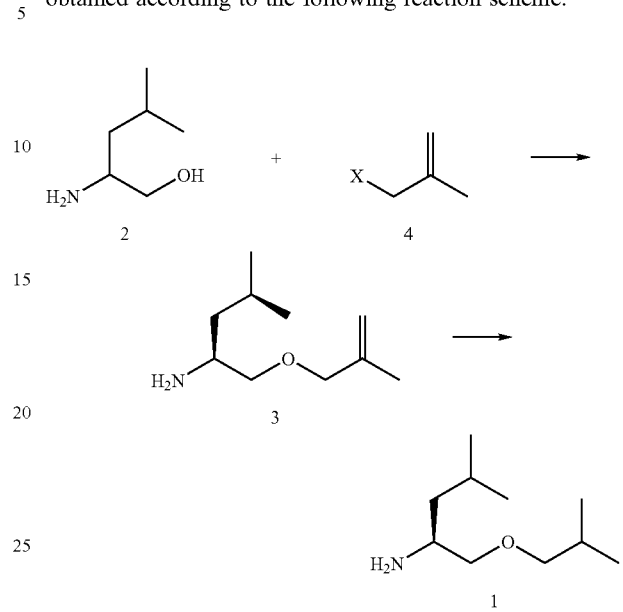

Step 1: L-leucinol (2)→Compound (3)

The reaction of L-leucinol (2) with the compound (4) can be performed in such a solvent not participating in the reaction as THF or DMSO at a temperature between −30° C. and the reflux temperature in the presence of a base.

Examples of the leaving groups represented by X in the compound (4) include halogens such as chlorine, bromine and iodine, p-toluenesulfonyloxy, and methanesulfonyloxy.

Examples of the bases include alkali metal hydrides such as NaH, LiH and KH, alkaline earth metal hydrides such as $CaH_2$, alkali metal alkoxides such as t-BuOK, inorganic bases such as NaOH and KOH, and organic bases such as triethylamine The starting compound, namely L-leucinol, can be obtained by reducing L-leucine (for example, U.S. Pat. No. 3,935,280).

Step 2: Compound (3)→Compound (1)

The reaction can be performed in such a solvent not participating in the reaction as ethanol or acetic acid at a hydrogen pressure of 1 to 100 atm., using 0.1 to 20% of such a catalyst employable for catalytic reduction of a double bond as Pd/C or Raney nickel.

The (1S)-1-isobutoxymethyl-3-methybutylamine also can be produced according to the following reaction scheme:

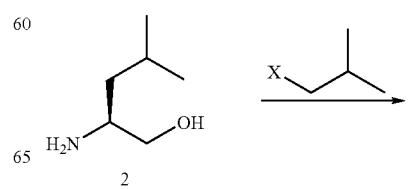

-continued

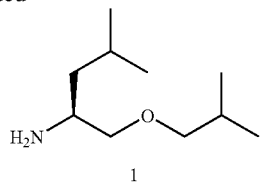

[in which X has the same leaving group as above].

The aforementioned Compound A can be produced from the (1S)-1-isobutoxymethyl-3-methylbutylamine obtained above according to the following reaction scheme (see Examples 48 and 18a of Patent reference 1):

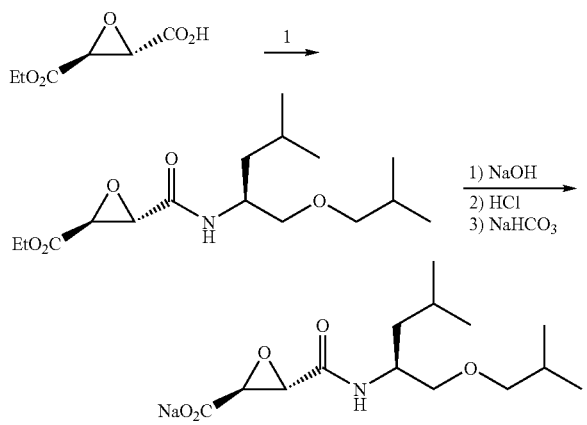

The process of the invention can give the amine derivative, i.e., (1S)-1-isobutoxymethyl-3-methylbutyl-amine, in a high yield. The aforementioned Compound A can be obtained from this amine derivative in a high yield.

The invention is further described by the following examples.

EXAMPLE 1

(1S)-1-(2-methyl-2-propenoxymethyl)-3-methyl-butylamine

To a solution of L-leucinol (20.0 g, 0.17 mol) in an anhydrous THF (200 mL) was portionwise added 60% NaH (7.92 g, 0.198 mol). The resulting mixture was stirred for 30 min. at room temperature and further for 2 hours at 50° C. The mixture was then cooled to room temperature. To the resulting suspension was dropwise added a solution of 3-chloro-2-methylpropene (15.45 g, 0.17 mol) in an anhydrous THF (50 mL). The resulting mixture was stirred for 20 hours at room temperature. The THF was distilled off under reduced pressure. To the residue were successively added a mixture of ice and water and diethyl ether. The mixture was stirred for 5 min. at room temperature, and the organic portion was separated. The aqueous portion was subjected to extraction with diethyl ether. The extract was combined with the organic portion. The combined organic portion was washed with 1 mol/L aqueous hydrochloric acid (7 mL) and subjected to extraction with 1 mol/L aqueous hydrochloric acid (153 mL). The resulting hydrochloric acid extract was made to approx. pH 10 by addition of potassium carbonate and subjected to extraction with diethyl ether. The organic portion was washed with water, dried over sodium sulfate, and placed under reduced pressure to distill the solvent off. There was obtained the titled compound (20.22 g, 69.2%) as an oily product.

$^1$H-NMR (CDCl$_3$) δ: 0.90 (3H, d, J=7 Hz), 0.93 (3H, d, J=7 Hz), 1.1–1.3 (2H, m), 1.74 (3H, s), 1.7–1.8 (1H, m), 2.62 (2H, broad s), 3.0–3.1 (1H, m), 3.15 (1H, dd, J=8 Hz & 9 Hz), 3.38 (1H, dd, J=3 Hz & 9 Hz), 3.88 (1H, d, J=13 Hz), 3.92 (1H, d, J=13 Hz), 4.89 (1H, s), 4.96 (1H, s).

EXAMPLE 2

(1S)-1-Isobutoxymethyl-3-methylbutylamine

A suspension of (1S)-1-(2-methyl-2-propenoxymethyl)-3-methylbutylamine (51.9 g, 0.3 mol) and 5% Pd/C (10.4 g) in ethanol (520 mL) was stirred for 18 hours at room temperature in a hydrogen atmosphere (1 atm.). To the resulting reaction mixture was added 6 mol/L aqueous hydrochloric acid (52 mL) under cooling in ice bath. The aqueous mixture was subjected to filtration using celite for removing insolubles and then placed under reduced pressure for distilling the solvent off. The residue was dissolved in water, and the resulting aqueous solution was made to approx. pH 10 by addition of potassium carbonate. The solution was subjected to extraction with diethyl ether. The organic portion was dried over sodium sulfate and placed under reduced pressure for distilling off the solvent. There was obtained the titled compound (48.6 g, 92.6%) as an oily compound.

bp: 66–67° C./5 mg $^1$H-NMR (CDCl$_3$) δ: 0.90 (3H, d, J=6 Hz), 0.90 (3H, d, J=6 Hz), 0.91 (3H, d, J=6 Hz), 0.93 (3H, d, J=6 Hz), 1.1–1.2 (2H, m), 1.50 (2H, broad s), 1.6–1.8 (1H, m), 1.8–1.9 (1H, m), 3.0–3.1 (1H, m), 3.11 (1H, dd, J=8 Hz & 9 Hz), 3.16 (1H, dd, J=7 Hz & 9 Hz), 3.23 (1H, dd, J=7 Hz & 9 Hz), 3.37 (1H, dd, J=3 Hz & 9 Hz).

What is claimed is:

1. (1S)-1-Isobutoxymethyl-3-methylbutylamine.

2. A process for preparing (1S)-1-isobutoxymethyl-3-methylbutylamine which comprises reducing (1S)-1-(2-methyl-2-propenoxymethyl)-3-methylbutylamine.

3. A process for preparing (1S)-1-isobutoxymethyl-3-methylbutylamine which comprises the steps of:

reacting L-leucinol and a compound having the following formula:

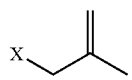

in which X is a leaving group, in the presence of a base, to give a (1S)-1-(2-methyl-2-propenoxymethyl)-3-methylbutylamine, and reducing the (1S)-1-(2-methyl-2-propenoxymethyl)-3-methylbutylamine.

* * * * *